(12) United States Patent
Chu et al.

(10) Patent No.: US 6,799,121 B2
(45) Date of Patent: Sep. 28, 2004

(54) SEQUENCING OF PEPTIDES BY MASS SPECTROMETRY

(75) Inventors: Ivan K. Chu, Toronto (CA); Tai-Chu Lau, Kowloon (HK); K. W. Michael Siu, Toronto (CA)

(73) Assignee: York University, Toronto (CA)

( * ) Notice: Subject to any disclaimer, the term of this patent is extended or adjusted under 35 U.S.C. 154(b) by 477 days.

(21) Appl. No.: 09/804,866

(22) Filed: Mar. 13, 2001

(65) Prior Publication Data

US 2002/0001814 A1 Jan. 3, 2002

Related U.S. Application Data

(60) Provisional application No. 60/193,208, filed on Mar. 30, 2000.

(51) Int. Cl.[7] .................. G01N 33/50; G01N 33/48; B01D 59/44
(52) U.S. Cl. .................. 702/20; 702/27; 530/300; 530/350; 250/281; 250/282; 250/283; 250/286; 250/287
(58) Field of Search .................. 702/20, 27; 530/300, 530/350; 250/281, 282, 283, 286, 287

(56) References Cited

PUBLICATIONS

Alexander, A.J.; Thibault, P.; Boyd, R.K.; Curtis, J.M.; Rinehart, K.L., "Collision Induced Dissociation of Peptide Ions", *Int. J. Mass Spectrom. Ion Processes*, 1990, 98, 107–134.

Ambihapathy, K.; Yalcin, T.; Leung, H.–W.; Harrison, A.G., "Pathways to Immonium Ions in the Fragmentation of Protonated Peptides", *J. Mass Spectrom.*, 1997, 32, 209–215.

Bouchonnet, S.; Hoppilliard, Y., "Proton and Sodium Ion of Affinities of Glycine and Its Sodium Salt in the Gas Phase. Ab Initio Calculations", *Org. Mass Spectrom.*, 1992, 27, 71–76.

Burlet, O.; Orkiszewski, R.S.; Ballard, K.D.; Gaskell, S.J., "Charge Promotion of Low–energy Fragmentations of Peptide Ions", *Rapid Commun. Mass Spectrom.*, 1992, 6, 658–662.

Cantor, C.R.; Schimmel, P.R., "Part 1: The Conformation of Biological Macromolecules", *Biophysical Chemistry*, W.H. Freeman and Co.: San Francisco, 1980, 275–307.

Chu, I.K.; Guo X.; Lau, T.–C.; Siu, K.W.M., "Sequencing of Argentinated Peptides by Means of Electrospray Tandem Mass Spectrometry", *Anal. Chem.*, 1999, 71, 2364–2372.

Cox, K.A.; Gaskell, S.J.; Morris, M.; Whiting, A., "Role of the Site of Protonation in the Low–Energy Decompositions of Gas–Phase Peptide Ions", *J. Am. Soc. Mass Spectrom.*, 1996, 7, 522–531.

Dawson, P.H.; French, J.B.; Buckley, J.A.; Douglas, D.J.; Simmons, D., "The Use of Triple Quadrupoles for Sequential Mass Spectrometry 1–The Instrument Parameters", *Org. Mass Spectrom.*, 1982, 17, 205–211.

Dawson, P.H.; French, J.B.; Buckley, J.A.; Douglas, D.J.; Simmons, D., "The Use of Triple Quadrupoles for Sequential Mass Spectrometry 2–A Detailed Case Study", *Org. Mass Spectrom.*, 1982, 17, 212–217.

Deng, H.; Kebarle, P.J., "Binding Energies of Silver Ion–Ligand, L, Complexes $AgL_2+$ Determined from Ligand–Exchange Equilibria in the Gas Phase", *Phys. Chem.* A 1998, 102, 571–579.

Dongré, A.R.; Somogyi, Á.; Wysocki, V.H., "Surface–induced Dissociation: An Effective Tool to Probe Structure, Energetics and Fragmentation Mechanisms of Protonated Peptides", *J. Mass Spectrom.*, 1996, 31, 339–350.

Dongré, A.R.; Jones, J.L.; Somogyi, Á.; Wysocki, V.H., "Inluence of Peptide Composition, Gas–Phase Basicity, and Chemical Modification on Fragmentation Efficiency: Evidence for the Mobile Proton Model", *J. Am. Chem. Soc.*, 1996, 118, 8365–8374.

Edman, P., "Sequence Determination", *Mol. Biol. Biochem. Biophys.*, 1970, 8, 211–255.

Fenn, J.B.; Mann, M.; Meng, C.K.; Wong, S.F.; Whitehouse, C.M., "Electrospray Ionization for Mass Spectrometry of Large Biomolecules", *Science*, 1989, 246, 64–71.

Figeys, D.; van Oostveen, I.; Ducret A.; Aebersold, R., Protein Identification by Capillary Zone Electrophoresis/Microelectrospray Ionization–Tandem Mass Spectrometry at the Subfemtomole Level, *Anal. Chem.* 1996, 68, 1822–1828.

Grese, R.P.; Cemy, R.L.; Gross, M.L., "Metal Ion–Peptide Interactions in the Gas Phase: A Tandem Mass Spectrometry Study of Alkali Metal Cationized Peptides", *J. Am. Chem. Soc.*, 1989, 111, 2835–2842.

Grese, R.P.; Cemy, R.L.; Gross, M.L., "Gas–Phase Interactions of Lithium Ions and Dipeptides", *J. Am. Chem. Soc.*, 1990, 112, 5089–5104.

Hu, P.; Gross, M.L., "Strong Interactions of Anionic Peptides and Alkaline Earth Metal Ions: Metal–Ion–Bound Peptides in the Gas Phase", *J. Am. Chem. Soc.*, 1992, 114, 9153–9160.

(List continued on next page.)

*Primary Examiner*—Mary K. Zeman
(74) *Attorney, Agent, or Firm*—Merchant & Gould, P.C.

(57) ABSTRACT

A strategy for semiautomatic sequencing of argentinated (silver-containing) oligopeptides is described. The method of sequencing described is based on a search algorithm that identifies a triplet peak relationship in a product ion spectrum of the $[M+Ag]^+$ ion of an oligopeptide. The ions that constitute a triplet are $[b_n+OH+Ag]^+$, $[b_n-H+Ag]^+$, and $[a_n-H+Ag]^+$, which are separated by 18 and 28 m/z units, respectively. The difference in the m/z values of adjacent triplets identifies the residue that is "cleaved". Observation of the $[y_n+H+Ag]^+$ ion containing the cleaved residue confirms the assignment.

15 Claims, 17 Drawing Sheets

OTHER PUBLICATIONS

Hu, P.; Gross, M.L., "Gas–Phase Anionic Complexes of Alkali Metal Ions and Peptides: Structure and Collision Activated Decompositions", *J. Am. Soc. Mass Specrom.*, 1993, 5, 137–143.

Hu, P.; Gross, M.L., "Gas–Phase Interactions of Transition–Metal Ions and Di– and Tripeptides: A comparision with Alkaline–Earth–Metal–Ion Interactions",*J. Am. Chem. Soc.*, 1993, 115, 8821–8828.

Hunt, D.F.; Yates, J.R., III; Shabanowitz, J.; Winston, S.; Hauer, C.R., "Protein sequencing by tandem mass spectrometry", *Proc. Natl. Acad. Sci.*, 1986, 83, 6233–6237.

Johnson, R.S., Martin, S.A., Bieman, K., "Collision–Induced Fragmentation of $(M+H)^+$ Ions of Peptides.Side Chain Specific Sequence Ions", *Int. J. Mass Spectrom. Ion Processes*, 1988, 86, 137–154.

Jones, J.L.; Dongré, A.R.; Somogyi, Á.; Wysocki, V.H., "Sequence Dependence of Peptide Fragmentation Efficiency Curves Determined by Electrospray Ionization/Surface–Induced Dissociation Mass Spectrometry",*J. Am. Soc. Chem.*, 1994, 116, 8368–8369.

Klassen, J.S.; Anderson, S.G.; Blades, A. T.; Kebarle, P., "Reaction Enthalpies for $M^+L = M^+ + L$, Where $M^+ = Na^+$ and $K^+$ and L = Acetamide, N–Methylacetamide, N, N–Dimethylacetamide, Glycine, and Glycyglycine, from Determinations of the Collision–Induced Dissociation Thresholds", *J. Phys. Chem.* 1996, 100, 14218–14227.

Leary, J. A.; Williams, T.D.; Bott, G., "Strategy for Sequencing Peptides as Mono– and Dilithiated Adducts Using a Hybrid Tandem Mass Spectrometer", *Rapid Commun. Mass Spectrom.*, 1989, 3, 192–196.

Leary, J.A.; Zhou, Z.; Ogden, S.A.; Williams, T.D., "Investigations of Gas–Phase Lithium–Peptide Adducts: Tandem Mass Spectrometry and Semiempirical Studies",*J. Am. Soc. Mass Spectrom.*, 1990, 1, 473–480.

Lee, S.–W.; Kim, H.S.; Beauchamp, J.L., "Salt Bridge Chemistry Applied to Gas–Phase Peptide Sequencing: Selective Fragmentation of Sodiated Gas–Phase Peptide Ions Adjacent to Aspartic Acid Residues", *J. Am. Chem. Soc.*, 1998, 120, 3188–3195.

Lee, V.W.–M.; Li, H.; Lau, T.–C.; Guevremont, R.; Siu, K.W.M., "Relative Silver(I) Ion Binding Energies of α–Amino Acids: A Determination by Means of the Kinetic Method", *J. Am. Soc. Mass Spectrom.*, 1988, 9, 760–766.

Lee, V.W.–M.; Li, H.; Lau, T.–C.; Siu, K.W.M., "Structures of b and a Product Ions from the Fragmentation of Argentinated Peptides",*J. Am. Chem. Soc.*, 1998, 120, 7302–7309.

Li, H.; Siu, K.W.M.; Guevremont, R.; Le Blanc, J.C.Y., "Complexes of Silver (I) With Peptides and Proteins as Produced in Electrospray Mass Spectrometry", *J. Am. Soc. Mass Spectrom.* 1997, 8, 781–792.

Matsudaira, P., Ed. *A Practical Guide to Protein and Peptide Purification for Microsequencing*, $2^{nd}$ ed.; Academic Press: San Diego, 1993; pp. 37–39.

McCormack, A.L.; Somogyi, Á.; Dongré, A.R.; Wysocki, V.H., "Fragmentation of Protonated Peptides: Surfaces–Induced Dissociation in Conjunction with a Quantum Mechanical Approach",*Anal. Chem.*, 1993, 65, 2859–2872.

McLafferty, F.W., "Tandem Mass Spectrometry", *Science*, 1981, 214, 280–287.

Narula, S.S.; Mehra, R.K.; Winge, D.R.; Armitage, I.M., "Establishment of the Metal–to–Cysteine Connectivities in Silver–Substituted Yeast Metallothionein", *J. Am. Chem. Soc.*, 1991, 113, 9354–9358.

Nold, M.J.; Wesdemiotis, C.; Yalcin, T.; Harrison, A.G., "Amide bond dissociation in protonated peptides. Structures of the N–terminal ionic and neutral fragments", *Int. J. Mass Spectrom. Ion Processes*, 1997, 164, 137–153.

Papayannopoulos, I.A., "The Interpretation of Collision–Induced Dissociation Tandem Mass Spectra of Peptides", *Mass Spectrom. Rev.*, 1995, 14, 49–73.

Renner, D.; Spiteller, G., "Linked Scan Investigation of Peptide Degradation Initiated by Liquid Secondary Ion Mass Spectrometry", *Biol. Environ. Mass Spectrom.*, 1988, 15, 75–77.

Shevchenko, A.; Jensen, O.N.; Podtelejnikov, A.V.; Sagliocco, F.; Wilm, M.; Vorm, O.; Mortensen, P.; Shevchenko, A.; Boucherie, H.; Mann, M., "Linking genome and proteome by mass spectrometry: Large–scale identification of yeast proteins from two dimensional gels", *Proc. Natl. Acad. Sci. U.S.A.*, 1996, 93, 14440–14445.

Smith, R.D.; Loo, J.A.; Ogorzalek Loo, R.R.; Busman, M.; Udseth, H.R., "Principles and practice of electrospray ionization–mass spectrometry for large polypeptides and proteins", *Mass Spectrom. Rev.*, 1991, 10, 359–451.

Stillman, M.J.; Presta, A.; Gui, Z.; Jiang, D.–T., *Metal–Based Drugs*; Gielen, M., Ed.; Freund: London, 1994; vol. 1, 375–393.

Summerfield, S.G.; Whitting, A.; Gaskell, S.J., "Intra–ionic interactions in electrosprayed peptide ions", *Int. J. Mass Spectrom. Ion Processes*, 1997, 162, 149–161.

Tang, X.; Ens, W.; Standing, K.G.; Westmore. J.B., "Daughter Ion Mass Spectra from Cationized Molecules of Small Oligopeptides in a Reflecting Time–of–Flight Mass Spectrometer", *Anal. Chem.*, 1988, 60, 1791–1799.

Tang, X.–J.; Thibault, P.; Boyd, R.K., "Fragmentation Reactions of Multiply–Protonated Peptides and Implications for Sequencing by Tandem Mass Spectrometry with Low–Energy Collision–Induced Dissociation", *Anal. Chem.*, 1993, 65, 2824–2834.

Teesch, L.M.; Adams, J., "Intrinsic Interactions between Alkaline–Earth Metal Ions and Peptides: A Gas–Phase Study", *J. Am. Chem. Soc.*, 1990, 112, 4110–4120.

Teesch, L.M.; Adams, J., "Fragmentation of Gas–Phased Complexes between Alkali Metal Ions and Peptides: Metal Ion Binding to Carbonyl Oxygens and Other Neutral Functional Groups", *J. Am. Chem. Soc.*, 1991, 113, 812–820.

Teesch, L.M.; Orlando, R.C.; Adams, J., "Location of the Alkali Metal Ion in Gas–Phase Peptide Complexes", *J. Am. Chem. Soc.*, 1991, 113, 3668–3675.

Wilm, M.S.; Mann, M., "Electrospray and Taylor–Cone theory, Dole's beam of macromolecules at last?", *Int. J. Mass Spectrom. Ion Proc.*, 1994, 136, 167–180.

Yalcin, T.; Khouw, C.; Csizmadia, I.G.; Peterson, M.R.; Harrison, A.G., "Why Are B Ions Stable Species in Peptide Spectra?",*J. Am. Soc. Mass Spectrom.*, 1995, 6, 1165–1174.

Yalcin, T.; Csizmadia, I.G., Peterson, M.R.; Harrison, A.G., "The Structure and Fragmentation of $B_n$ (n $\geqq$ 3) Ions in Peptide Spectra", *J. Am. Soc. Mass Spectrom.*, 1996, 7, 233–242.

Zhao, H.; Reiter, A.; Teesch, L.M.; Adams, J.; "Gas–Phase Fragmentations of Anionic Complexes between Peptides and Alkaline Earth Metal Ions: Structure–Specific Side–Chain Interactions", *J. Am. Chem. Soc.*, 1993, 115, 2854–2863.

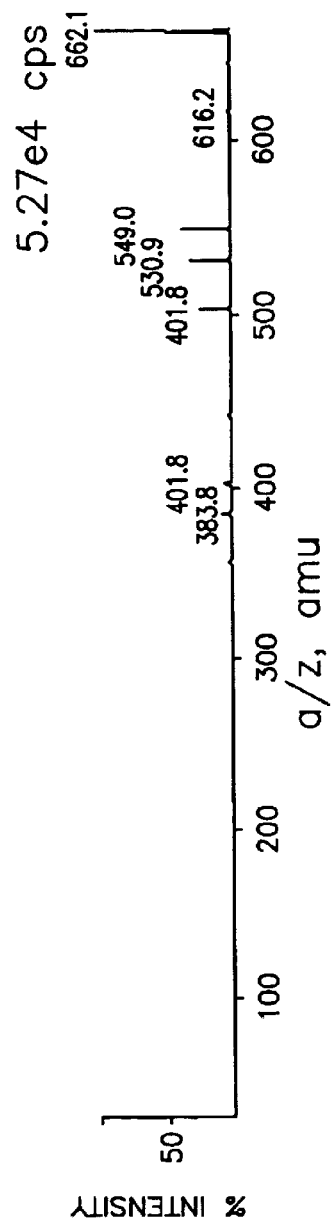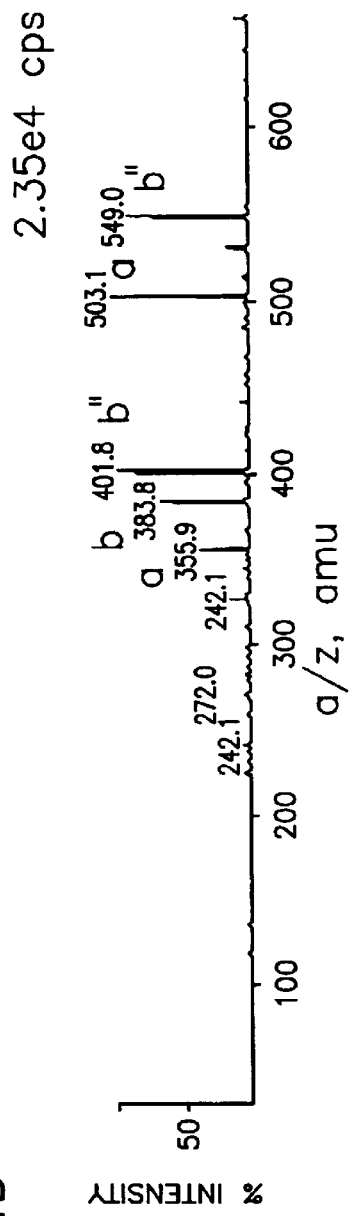

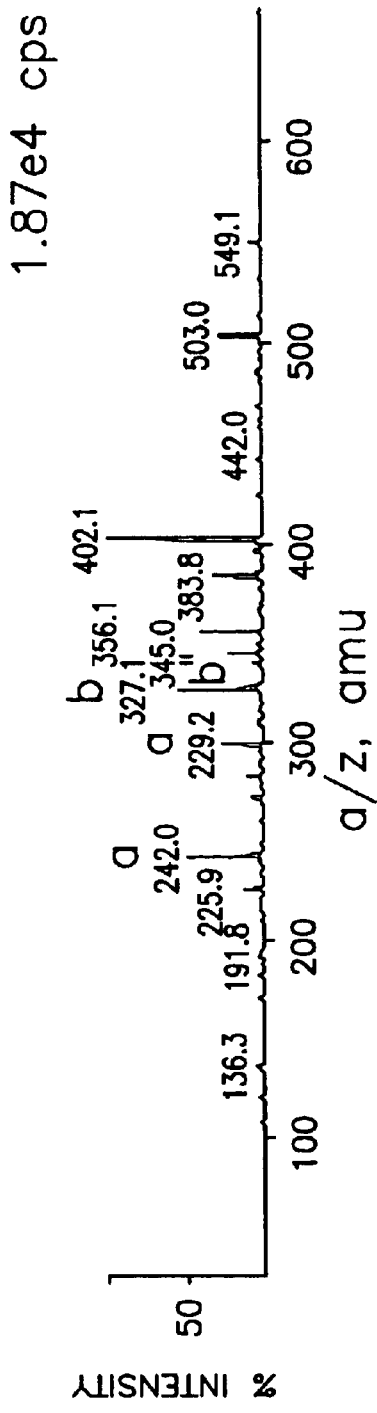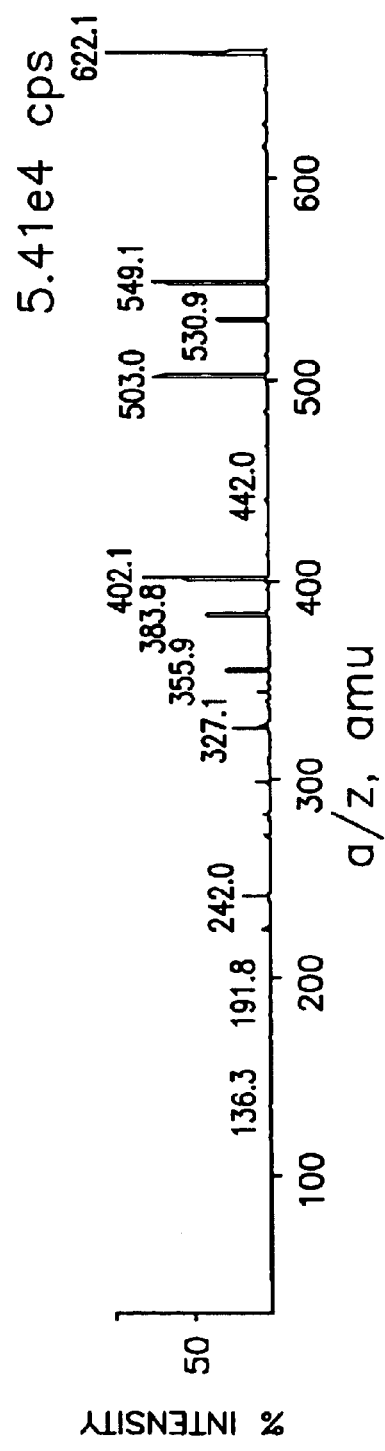

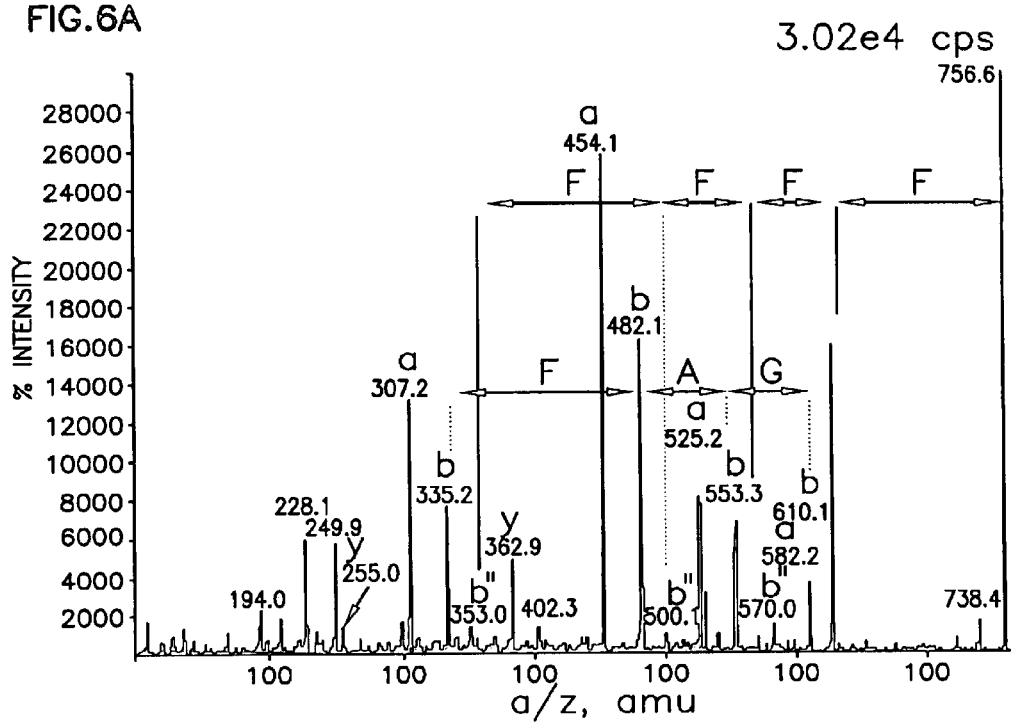
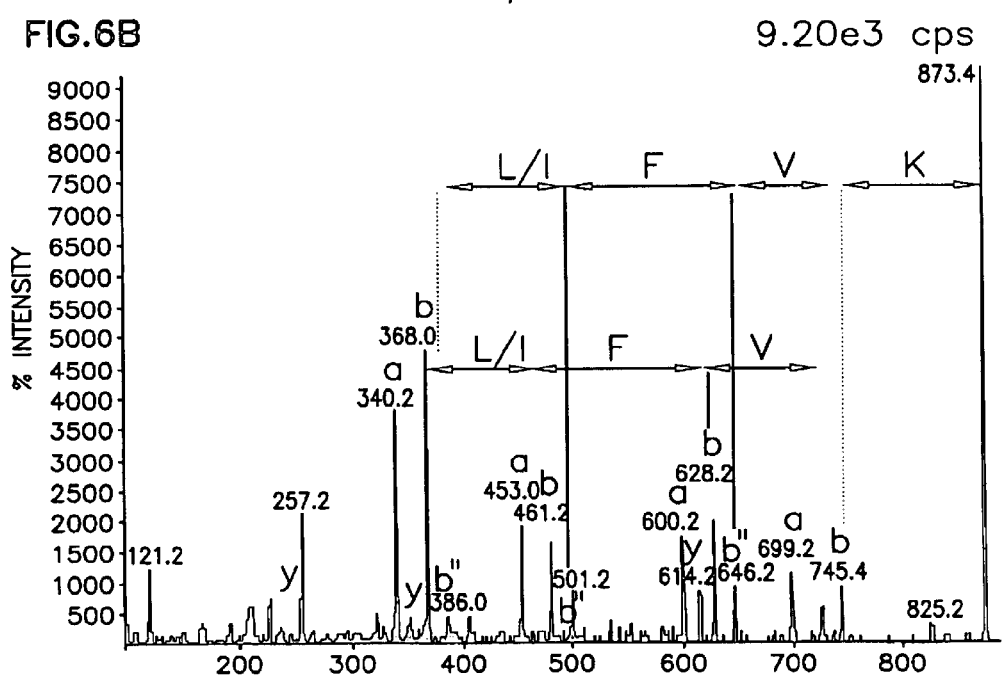

FIG.7A

Option Explicit

////////////////////////////////////////////////////////////////

////, Type Declaration

////////////////////////////////////////////////////////////////

////, Constant Declaration

Const ciFrmHeight As Integer = 5900   ////, Form height
Const ciFrmHeight As Integer = 9600   ////, Form height

////////////////////////////////////////////////////////////////

////, Variable Declaration

Dim icountFound As Integer          ////, No of series found

////////////////////////////////////////////////////////////////

////, Prototypes

////////////////////////////////////////////////////////////////

////, Funtion Declaration

Private Sub Form_Load()
    ////, Initialization
    Call P_LoadForm
End Sub

FIG.7B

```
////////////////////////////////////////////////////////////
////
//// Synopssis  :P_LoadFoam()
//// Name       :Private Sub P_LoadForm()
////
//// Input      :None
////
//// Return     :None
////////////////////////////////////////////////////////////
Private Sub P_LoadFoam()
    //// Label initialization
    lblFirstRow.Caption = " "
    lblFirstValue.Caption = " "
    lblSecondRow.Caption = " "
    lblSecondValue.Caption = " "
    lblThirdRow.Caption = " "
    lblThirdValue.Caption = " "

//// Parameters initialization
    'glErrCode = RC_SUCCESS
    'gsErrMsg = " "
End Sub
```

FIG.7C

```
Private Sub cmdOK_Click()
  Call P_FirstUpdate
End Sub

'////////////////////////////////////////////////////////////////
'////
'//// Synopssis   :P_FirstUpdate
'////
'//// Name        :Private Sub P_FirstUpdate()
'////
'//// Description :Update in the first form
'////
'//// Input       :None
'////
'//// Return      :None
'////
'////////////////////////////////////////////////////////////////
Private Sub P_FirstUpdate()
  Screen.MousePointer = vbHourglass
  'glErrCode = RC_SUCCESS
  Screen.MousePointer = vbDefault
  Call FindNoSeries
End Sub Private Sub cmdCancel_Click()
  Unload Me
  Exit Sub
End Sub Private Sub Form_Unload(Cancel AS Integer)
  '//// Clean up the form
  Call P_UnloadForm
End Sub
```

FIG.7D

```
////////////////////////////////////////////////////////
///.
///. Synopssis  :P_FirstUploadForm
///.
///. Name       :Private Sub P_UploadForm()
///.
///. Description :Release the resource which occupied by the parameters
///.                    in the form
///. Input      :None
///.
///. Return     :None
///.
////////////////////////////////////////////////////////
Private Sub P_UploadForm()

End Sub

////////////////////////////////////////////////////////
///.
///. Synopssis  :FindNoSeries
///.
///. Name       :FindNoSeries() As Long
///.
///. Description :Function to update Uex file and stock cosing price
///.
///. Input      :N/A
///.
///. Return     :FindNoSeries   RC_SUCCESS   Success
///.                            RC_ERROR     Error
///.
////////////////////////////////////////////////////////
Public Funtion FindNo Series() As Long
   Dim gsPath As String
   Dim gsCEFile As String
```

FIG.7E

```
Dim gsErrMsg As String
Dim gsExist As String
Dim takeFile As String
Dim giCEFileNo As Integer
Dim bCloseFileNo As Boolean
Dim sNextLn As String
Dim asNumberFound(800) As String
Dim sFileName As String
'FindNoSeries = RC_ERROR
bCloseFile = True
'gsErrMsg = " "

'gsPath = App.Path
//// Name of file is SortRecord
gsCEFILE = gsPath & "/" & "SortRecord" & "/"
sExit = Dir(gsCEFile)
sFileName = txtFileName.Text & ".txt"
If sExist = sFileName Then
    bCloseFile = False
End If If bCloseFileThen
    //// "not found. Update process not proceeded."
    gsErrMsg = "SortRecord not found. Process stops."
    MsgBox (gsErrMsg)
    'FindNoSeries = RC_ERROR
    Exit Function
End If giCEFileNo = FreeFile
takeFile = gsCEFile & sExist
Open takeFile For Input As #giCEFileNo Dim tlLnNum As Long
```

FIG.7F

```
ILnNum = 0
Line Input #giCEFileNo. sNextLn

Do Until UCase(Trim(sNextLn)) = "END"

//// Vailidation
    If EOF(giCEFileNo) Then
        //// "Unexpected end of file."
        gsErrMsg = "Unexpected end of file."
        MsgBox (gsErrMsg)
        'FindNo Series =RC_ERROR
        Exit Function
    End If
    If NotIsNumeric(sNexrLn) Then
        //// "Unexpected end of file."
        gsErrMsg = "Non-numeric input" & "Row" & ILnNum + 1 & "."
        MsgBox (gsErrMsg)
        'FindNoSeries = RC_ERROR
        Exit Function
    End If
    If ILnNum <> 0 Then
     If Val(asNumberFound(ILnNum - 1)) < Val(sNextLn) Then
        gsErrMsg = "The input numbers are not sorted.(at row" & ILnNum + 1 & ".)"
        MsgBox (gsErrMsg)
        'FindNoSeries = RC_ERROR
        Exit Function
     End If
    End If
    asNuberFound(ILnNum) = SNextLn DoEvents
    Line Input #giCEFileNo. SnextLn
    ILnNum = (ILnNum +1)
Loop
```

FIG.7F

If Not EOF(giFileNo) Then

////. "Unexpected end of file"

gsErrMsg = "unexpected end of file"

MsgBox (gsErrMsg)

'FindNoSeries = RC_ERROR

Exit Function

End If

Close #giCEFileNo

Dim lPrimaryNo As String

Dim LsecondaryNo As String

Dim lTotalNo As String

Dim iOuterLoop As Integer

Dim iInnerLoop As Integer

Dim bFound As Boolean

Dim bNotFound As Boolean

Dim lMagicNo As String

Dim lTolNo As String

Dim lMagicOne As String

Dim lMagicTwo As String

Dim lTolOne As String

Dim lTolTwo As String

Dim asNumberOuput(200) As Long

Dim iCountOutput As Integer

Dim iFileNum As Integer

Dim putFile As String bCloseFile = True

////. "Unexpected end of file"

'gsPath = App.Path

////. Name of file is SortRecord gsCEFile = gsPath & "/" & "Result" & "/"

FIG.7H

```
'sExist = Dir(gsCEFile)
'If sExist = "Try I .txt"
   bCloseFile = False
'End If If bCloseFileThen
   //// "not found. Update process not proceeding."
   gsErrMsg = "Result not found. Process stops."
   MsgBox (gsErrMsg)
   'FindNoSeries = RC_ERROR
   Exit Function
End If //// Open file for writing result
iFileNum = FreeFile
putFile = App.Path & "\" & "Result & "\" & txtFileName.Text & ".txt"
Open putFile For Append as #iFileNum //// Set initial value
iCountFound = 0
clMagicOne = Vai(txtDiff1.Text)
clMagicTwo = Vai(txtDiff2.Text)
clTolOne = Vai(txtTol1.Text)
clTolTwo = Vai(txtTol2.Text)
bFound = False
bNotFound = False
iCountOuput = 0
iMagicNo = clMagicOne
iTotalNo = ILnNum
For iOuterLoop = 0 To (ITotalNo - 1)
   IPrimaryNo = asNumberFound(iOuterLoop)
   //// Set all captions
   lblFirstValue.Caption = IPrimaryNo
   lblFirstRow.Caption = liOuterLoop = 1
```

FIG.7I

```
lblSecondValue.Caption = " "
lblSecondRow.Caption = " "
lblThirdValue.Caption = " "
lblThirdRow.Caption = " "
//// Reset variable in interloop
    bFound = False
    bNotFound = False
    iMagicNo = clMagicOne
    iTolNo = lLnNum
//// set interloop begin value
iInnerloop = iOuterLoop = l
//// do until end of list or pattern found or not found
Do until BFound Or bNotFound Or (iInnerloop > lTotal - 1)
    lSecondaryNo = asNumbersFound(iInnerLoop)
    If (Val(PrimaryNo) - Val(SecondaryNo)) .= (Val(MagicNo) - Val(lTolNo)) And_
    (Val(PrimaryNo) - Val(SecondaryNo)) .= (Val(MagicNo) - Val(lTolNo)) And_
        If lMagicNo = clMagicTwo Then
        lblThirdValue.Caption = lSecondaryNo
        lblThirdRow.Caption = iInnerLoop + 1
        bFound = True
        'FindNoSeries = RC_SUCCESS
        Write #iFileNum, lPRimaryNo & "&" & lSecond & _
            "&" & lSecondaryNo Write #iFileNum, lPRimaryNo & "&" & lSecond & "&" & lSecondaryNo
            '((lPrimaryNo - 18 + lSecond + lSeconaryNo +28) / 3
        iCountFound = iCountFound +1
    Else
        lblSecondValue.Coupon = lSecondaryNo
        lblSecondRow.Coupon = iInnerLoop + 1
        lSecond = lSecondaryNo
        lMagicNo = clMagicTwo
    End If
ElseIf (Val(SecondaryNo) - Val(PrimaryNo)) > Val(MagicNO) Then
```

FIG.7J

```
        BNotFound = True
    End If
    iInnerLoop = iInnerLoop + 1
Next
//// Close file
    Close #iFileNum If bFound = False Then
    'FindNoSeries = RC_NOT_FOUND
    End If If iCountFound <> 0 Then
        lblTrueFalse.Caption = "True"
        MsgBox (iCountFound & "specific series number are found and save in
"&" txtFileName.Text & ".txt)
    Else
        lblTrueFalse.Caption = "False"
        MsgBox ("The specific series number is not found!!!")
    End If
End Function
```

SEQUENCING OF PEPTIDES BY MASS SPECTROMETRY

This application claims priority under 35 U.S.C. §119(e) to U.S. provisional patent application 60/193,208 filed Mar. 30, 2000.

FIELD OF THE INVENTION

This invention relates to methods of protein analysis and more particularly concerns methods of sequencing oligopeptides.

BACKGROUND OF THE INVENTION

Identifying the sequence of amino acid residues in a protein is often the first step in a study of the function of an unknown protein. This is traditionally accomplished by means of Edman degradation (Edman (1970)) Despite being a time-honored method, Edman sequencing has a major disadvantage in that it requires, typically, milligram quantities of a protein, an amount often considered excessive in today's laboratory practice and standards. Gas-phase microsequencing by means of tandem mass spectrometry has increasingly been applied to obtain partial, or even complete, sequences of unknown peptides (Hunt et al. (1986); Johnson et al. (1988); Papayannopoulos (1995)). In the last couple of years, a major application of the above has been in the area of proteome analysis, where partial sequences of enzymatically cleaved peptides have been used for the purpose of protein identification via the so-called "sequence tag" method (Shevchenko et al. (1996); Figeys et al. (1996)). Mass spectrometry's major advantages in chemical analysis have been well-documented (McLafferty (1981)) and are applicable to peptide sequencing.

A protonated peptide, produced by means of electrospray (Fenn et al. (1989), fragments typically under low-energy ($\leq 100$ eV) tandem mass spectrometric conditions to yield product ions that are indicative of the amino acid residue sequence (Hunt et al. (1986); Johnson et al. (1988); Papayannopoulos (1995)). In solution, the most basic sites on a peptide are the nitrogen atoms at the N-terminal amino group and the side chains of the histidine, lysine, and arginine residues (Cantor et al. (1980); Smith et al. (1991)). However, once the protonated peptide ion has been desorbed into the gas phase, transfer of the "external" proton, particularly after collisional activation, to amidic functional groups, the carbonyl oxygen and the amidic nitrogen atoms, on the backbone becomes possible (McCormack et al. (1993); Jones et al. (1994); Dongré et al. (*Mass Spectrom.* 1996); Dongré et al. (*J. Am. Chem. Soc.* 1996). The peptide then fragments at the protonated peptide linkage to yield an ionic and a neutral fragment. If the charge is retained on the N-terminal fragment, a b ion is produced; the b ion may subsequently lose CO to form the a ion. Alternatively, if the charge is retained on the C-terminal fragment, a y" (y+2H) ion is produced (Hunt et al. (1986); Johnson et al. (1988); Papayannopoulos (1995); McCormack et al. (1993); Jones et al. (1994); Dongré et al. (*Mass Spectrom.* 1996); Dongré et al. (*J. Am. Chem. Soc.* 1996). Results from a series of studies have shown that the b ion has an oxazolone structure (Yalcin et al. (1995); Yalcon et al. (1996); Ambihapathy et al. (1997); Nold et al. (1997)), the a ion is an immonium ion, and the y" ion is a protonated peptide or amino acid (Hunt et al. (1986); Johnson et al. (1988); Papayannopoulos (1995); McCormack et al. (1993); Jones et al. (1994); Dongré et al. (*Mass Spectrom.* 1996); Dongré et al. (*J. Am. Chem. Soc.* 1996). A product-ion spectrum of a protonated peptide typically consists of series of b, a, and y" ions which reflect the amino acid sequence. Unfortunately, the fragmentation chemistry of a peptide is rich, and there may be gaps in the series of product ions; this makes sequencing non-routine to all but the highly experienced.

The fragmentation of alkali- and alkaline-metal containing peptides in tandem mass spectrometry has been a subject of much interest and study (Renner et al. (1988); Grese et al. (1989); Grese et al. (1990); Hu et al. (1992); Hu et al. (*J. Am Soc. Mass Spectrom.* 1993); Hu et al. (*J. Am. Chem. Soc.* 1993); Tang et al. (1988); Teesch et al. (1990); Teesch et al. (*J. Am. Chem. Soc.* 113, 812–820 (1991)); Teesch et al. *J. Am. Chem. Soc.*, 113, 3668–3675 (1991); Zhao et al. (1993); Leary et al. (1989); Leary et al. (1990); Lee et al. (1998)). Although most of these reports concentrated on examination of the structures of metal-containing product ions and the mechanisms of their formation (Renner et al. (1988); Grese et al. (1989); Grese et al. (1990); Hu et al. (1992); Hu et al. (*J. Am Soc. Mass Spectrom.* 1993); Hu et al. (*J. Am. Chem. Soc.* 1993); Tang et al. (1988); Teesch et al. (1990); Teesch et al. (*J. Am. Chem. Soc.* 113, 812–820 (1991)); Teesch et al. (*J. Am. Chem. Soc.*, 113, 3668–3675 (1991); Zhao et al. (1993); Leary et al. (1989); Leary et al. (1990); Lee et al. (1998)), the potential for acquiring sequence information from metal-containing, e.g., lithiated and sodiated, peptides was readily apparent irrespective of whether that was implied or explicitly stated (Leary et al. (1989)). Unlike protonated peptides, lithiated and sodiated peptides tend to fragment after collisional activation to yield primarily the $[b_n+OH+X]^+$ ions (X=Li or Na) (Renner et al. (1988); Grese et al. (1989); Grese et al. (1990); Tang et al. (1988); Teesch et al. (*J. Am. Chem. Soc.*, 113, 3668–3675 (1991); Lee et al. (1998)). These product ions are believed to form from elimination of C-terminal residues from precursor ion structures in which the alkali-metal ion is bound to the C-terminal carboxylate anion of a zwitterionic peptide. Rearrangement as a result of collisional activation results in transfer of the C-terminal OX group to the carbonyl carbon of the preceding residue and elimination of CO and an imine (Renner et al. (1988); Grese et al. (1989); Grese et al. (1990); Lee et ala. (1998)). Unfortunately, the affinities of peptides for the lithium and the sodium ions are weak relative to those for the proton (Bouchonnet et al. (1992); Klassen et al. (1996)); consequently, cleavage of the metal ion is often a more favorable fragmentation pathway relative to backbone fragmentation and leads to low yields in these more sequence-informative reactions.

SUMMARY OF THE INVENTION

The present inventors have found that they are able to determine the sequences of peptides or proteins by analysing the peptides or proteins in argentinated form using mass spectrometry.

Accordingly the present invention provides a method of analyzing argentinated peptides or proteins using mass spectrometry comprising:

(a) combining an oligopeptide with silver to provide a sample comprising argentiated oligopeptide;

(b) submitting the sample to a mass spectrometer;

(c) performing scans of silver containing peaks in optimum collision energies;

(d) identifying any doublet or triplet peak pattern;

(e) confirming with Y ions;

(f) determining partial sequence by the mass separation between two successive doublet or triplet patterns.

Preferably the oligopeptide comprises from about 3 to about 10 amino acids and the performing scans comprise collecting product ion spectra of the [M+Ag]$^+$ ion, where M=oligopeptide;

According to a preferred embodiment, the method of the invention utilizes silver nitrate.

According to another embodiment of the method of the invention according the determination of partial sequence comprises searching for, and identifying cleaved amino acid residues based on differences in m/z values of neighboring triplets where the m/z value of the [b$_n$–H+Ag]$^+$ ion and the corresponding [y$_n$+H+Ag]$^+$ ion are related by the formula: [y$_n$+H+Ag]$^+$=[M+Ag]$^+$+Ag$^+$–[b$_n$–H+Ag]$^+$. Preferably the searching and identifying is conducted by a custom search algorithm, more preferably the algorithm is written in Visual Basic and looks for the triplet peak pattern of (m/z)$_1$, (m/z)$_2$)=(m/z)$_1$–18.0, and (m/z)$_3$=(m/z)$_2$–28.0 as well as the doublet pattern of (m/z)$_2$ and (m/z)3, all to within ±0.5 m/z unit.

According to yet another embodiment of the method the product ion spectra of the [M+Ag]$^+$ ion are collected under E$_{cm}$s, of 1.5, 2.0, 2.5 and 3.0 eV.

According to a further embodiment of the invention the method the mass spectrometer of the method is a triple quadrupole mass spectrometer, two triple quadrupole mass spectrometers, a quadrupole/time-of-flight mass spectrometer, an ion-trap mass spectrometer, or a time-of-flight mass spectrometer amenable to post-source decay or collision-induced dissociation.

According to another embodiment the method according to the present invention comprises:

(a) combining an oligopeptide with silver nitrate in solution;

(b) submitting a sample of the solution to a mass spectrometer;

(c) collecting product ion spectra of the [M+Ag]$^+$ ion, where M=oligopeptide;

(d) identifying the triplet peak pattern;

(e) identifying the doublet peak pattern;

(f) searching for, and identifying cleaved amino acid residues based on differences in m/z values of neighboring triplets where the m/z value of the [b$_n$–H+Ag]$^+$ ion and the corresponding [y$_n$+H+Ag]$^+$ ion are related by the formula: [y$_n$+H+Ag]$^+$=[M+Ag]$^+$+Ag$^+$–[b$_n$–H+Ag]$^+$. Preferably the oligopeptide comprises from about 3 to about 10 amino acids.

According to a preferred embodiment according to this method the searching and identifying is conducted by a custom search algorithm, preferably the algorithm is written in Visual Basic and looks for the triplet peak pattern of (m/z)$_1$, (m/z)$_2$)=(m/z)$_1$18.0, and (m/z)$_3$=(m/z)$_2$–28.0 as well as the doublet pattern of (m/z)$_2$ and (m/z)3, all to within ±0.5 m/z unit. More preferably the product ion spectra of the [M+Ag]$^+$ ion are collected under E$_{cm}$s, of 1.5, 2.0, 2.5 and 3.0 eV. Preferably the mass spectrometer used according to the method of the invention is a triple quadrupole mass spectrometer or two triple quadrupole mass spectrometers, however, any mass spectrometer capable of tandem mass spectrometry, such as a quadrupole/time-of-flight mass spectrometer, an ion-trap mass spectrometer, or a time-of-flight mass spectrometer amenable to post-source decay or collision-induced dissociation, may be used.

Other features and advantages of the present invention will become apparent from the following detailed description. It should be understood, however, that the detailed description and the specific examples while indicating preferred embodiments of the invention are given by way of illustration only, since various changes and modifications within the scope of the invention will become apparent to those skilled in the art from this detailed description.

DESCRIPTION OF THE DRAWINGS

The invention will now be described in relation to the drawings in which:

FIG. 1 shows product ion spectra of the [M+$^{107}$Ag]$^+$ ion of leucine enkephalin, YGGFL (SEQ. ID. NO. 1), at different E$_{cm}$s: (a) 1.5 eV, (b) 2.0 eV, (c) 2.5 eV, and (d) composite of (a) to (c). b*=[b$_n$+OH+Ag]$^+$, b=[b$_n$–H+Ag]$^+$, and a=[a$_n$–H+Ag]$^+$.

FIG. 6 shows the product-ion spectra of tryptic peptides at linear E$_{cm}$ functions (a) from 4.6 to 1.8 eV and (b) from 4.0 to 1.6 eV.

FIG. 7 shows a custom search algorithm of the invention written in Visual Basic.

DETAILED DESCRIPTION OF THE INVENTION

Figure 2:
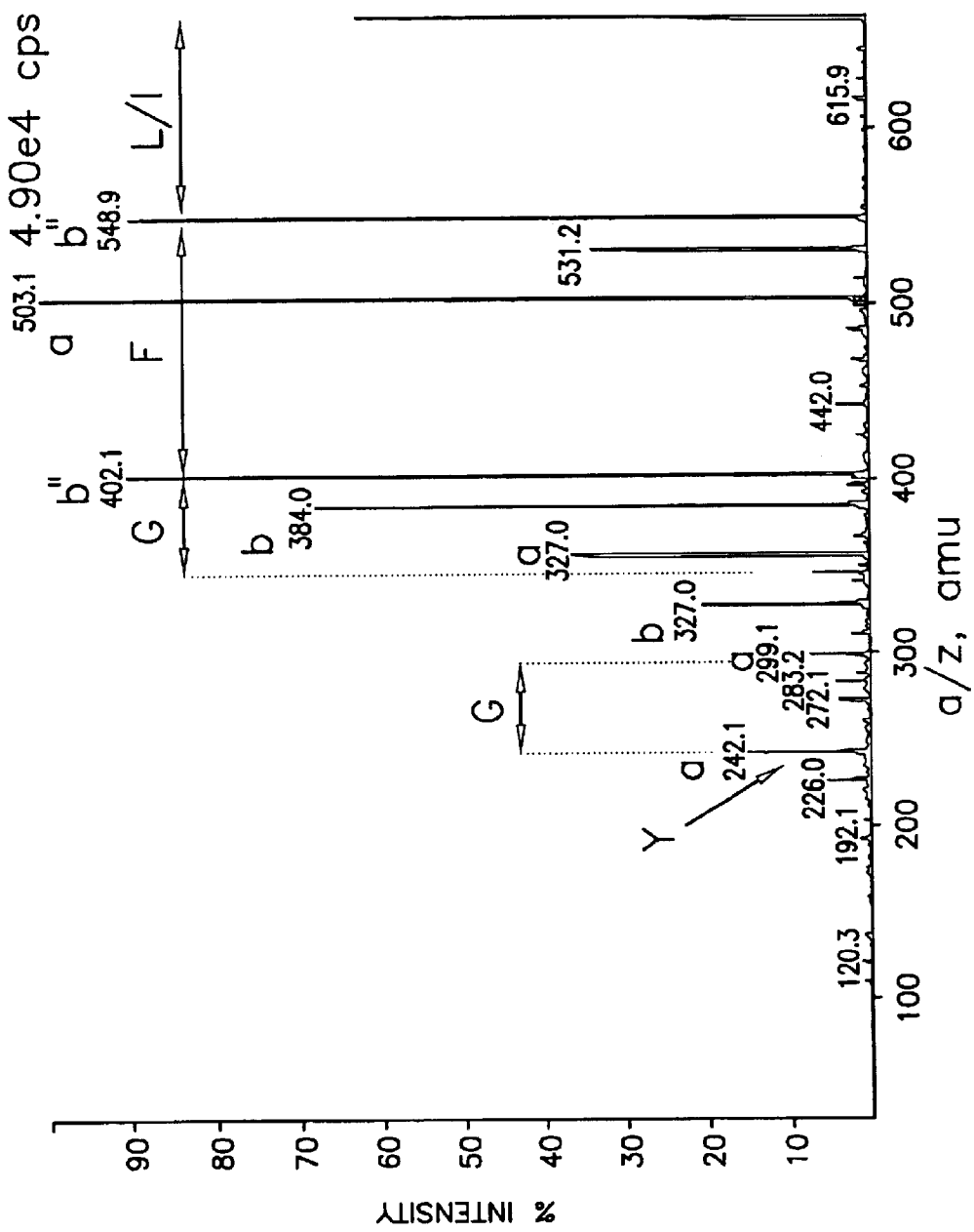
FIG. 2 shows a product-ion spectrum of the [M+$^{107}$Ag]$^+$ ion of leucine enkephalin, YGGFL (SEQ. ID. NO. 1), at a linear E$_{cm}$ function from 2.5 eV for m/z=30 to 1.5 eV for m/z=663.

As mentioned above, the present inventors have found that they are able to determine the sequences of peptides or proteins by analysing the peptides or proteins in argentinated form using mass spectrometry. In its broad aspect the invention provides a method of analyzing argentinated peptides or proteins using mass spectrometry comprising:

(a) combining an oligopeptide with silver to provide a sample comprising argentiated oligopeptide;

(b) submitting the sample to a mass spectrometer;

(c) performing; scans of silver containing peaks in optimum collision energies;

(d) identifying any doublet or triplet peak pattern;

(e) confirming with Y ions;

(f) determining partial sequence by the mass separation between two successive doublet or triplet patterns.

Mass Spectrometry

Although the data presented in the examples described herein were conducted on two triple quadrupole mass spectrometers on two triple quadrupole mass spectrometers, any mass spectrometers that are capable of tandem mass spectrometry, such as a quadrupole/time-of-flight mass spectrometer, an ion-trap mass spectrometer, or a time-of-flight mass spectrometer amenable to post-source decay or collision-induced dissociation, may also be used, with appropriate adjustments known to those skilled in the art. The ions may be generated by a number of methods including electrospray, MALDI (matrix-assisted laser desorption ionization) and FAB (fast-atom bombardment). The method of the invention can be applied to oligopeptides of any length, preferably the number of amino acid residues is between 3 and 20.

Where prepared oligopeptides of unknown sequence are to be analysed they are put into solution in 50/50 water/methanol with a 5:1 ratio of moles of silver: moles of peptide. The exact composition of the solution and the mole ratios are not crucial. The sequencing will work for solutions of pure methanol and pure water, and mole ratios of 1:1 to 100:1. Proteins of unknown sequence are preferably digested by methods known to those skilled in the art. For example, trypsin or other active protease is reacted with an optimum amount of protein substrate and digested to completion. As for oligopeptides sufficient silver (e.g., silver nitrate) is added to provide adequate binding for analysis.

Sequencing

The silver (I) ion is the preferred ion to be used as it exhibits relatively higher affinities than alkali-metal ions for nitrogen- and sulfur-containing small ligands that are representative of the functional groups that exist in amino acids and peptides (Narula et al. (1991); Stillman et al. (1994); Deng et al. (1998); Li et ala. (1997); Lee et al. (*J. Am. Soc. Mass Spectrom.* 1998); Lee et al. (*J. Am. Chem. Soc.* 1998)). While not preferred, alkali-metal ions in the method of the invention are included within the scope of the invention. Also within the scope of the invention are chemical equivalents of the silver ion, i.e., chemical compounds which are able to provide comparable results with those achieved with silver. As used herein, "silver" includes any source of silver, or source which is able to provide a silver-ion or chemical equivalent.

Electrospraying a peptide solution containing silver (I) typically yields an intense $[M+Ag]^+$ ion, which fragments efficiently under low-energy collision conditions to yield intense product ions that result from backbone fragmentation (Li et al. (1997); Lee et al. (*J. Am. Chem. Soc.* 1998)). These are the following: $[b_n-H+Ag]^+$, $[a_n-H+Ag]^+$, $[y_n+H+Ag]^+$, and $[b_n+OH+Ag]^+$ ions. The $[b_n-H+Ag]^+$ ion has been determined to be an N-argentinated oxazolone, whereas the $[a_n-H+Ag]^+$ an an N-argentinated immonium ion (Lee et al. (*J. Am. Chem. Soc.* 1998)). A fraction of the fragmenting $[b_n+OH+Ag]^+$ has been postulated to have a silver salt structure in which the $Ag^+$ ion is bound to the carboxylate anion of the zwitterionic peptide, although the most stable $[b_n+OH+Ag]^+$ structure is nonzwitterionic; the $[y_n+H+Ag]^+$ s an argentinated amino acid or truncated peptide (Chu et al. (not published)). For identical peptides, the product ions of $[M+Ag]^+$ are more intense than those of $[M+Na]^+$, and the relative intensities of the $[b_n+OH+Ag]^+$ ions are typically lower than those of the $[b_n+OH+Na]^+$ ions (Chu et al. (not published)). These observations are in line with the softer properties of $Ag^+$ relative to $Na^+$, and may be interpreted to result in relatively less prominent binding to the harder carboxylate terminus and more prominent binding to the softer N-terminal and amidic nitrogen atoms (Lee et al. (*J. Am. Chem. Soc.* 1998); Chu et al. (not published)). Accordingly, with an appropriate choice of collision energies, the $[b_n+OH+Ag]^+$, $[b_n-H+Ag]^+$, and $[a_n-H+Ag]^+$ ions of the same n can often be made to have abundances within a factor of 5 from one another (together with typically less abundant $[y_n+H+Ag]^+$ ions). From a sequencing point of view, this is convenient as the triplet peaks of $[b_n+OH+Ag]^+$, $[b_n-H+Ag]^+$ and $[a_n-H+Ag]^+$ ions are separated by a constant 18 and 28 m/z units. The triplets are easily recognizable in a search algorithm that identifies peaks of 18 and 28 m/z unit separation; the difference in m/z values of neighboring triplets identifies the amino acid residue that is cleaved. However, as will be readily understood by those skilled in the art, the invention is not so limited and includes within its scope recognition of any doublet or triplet pattern and searching on this basis.

Accordingly, in order to obtain sequence information, product-ion spectra of the $[M+Ag]^{30}$ ion collected under several $E_{cm}$, (for examples 1.5, 2.0, 2.5, and 3.0 eV, although other values may be used, values are chosen to provide as wide a range of abundant product ions as possible) and are summed to yield a composite spectrum. Such spectra exhibit a wide range of abundant product ions. Alternatively, product-ion spectra are acquired with an m/z dependent $E_{cm}$ function (typically linear) to maximize the number of observable sequence-relevant product ions. The peak abundance file of the spectrum for sequencing, after elimination of peaks below a certain user-defined threshold, typically 10%, are read into a custom search algorithm written in Visual Basic (see FIG. 7) which looks for the triplet peak pattern of $(m/z)_1$, $(m/z)_2=(m/z)_1-18.0$, and $(m/z)_3=(m/z)_2-28.0$ as well as the doublet pattern of $(m/z)_2$ and $(m/z)_3$, all to within±0.5 m/z unit. Triplet and doubler peak pattern that are found are imported into any commercially available spreadsheet program, for example, Excel. A user-defined threshold is used to filter out noise. This user-defined threshold can be from 1 to 20% of maximum however, a preferred threshold is 10% of maximum. The differences in m/z values of neighboring triplets are used to search for cleaved amino acid residues or combinations of them by means of AminoCal, a shareware available on the World Wide Web (protana.com/sofiware/default.asp) The use of the spreadsheet program and AminoCal facilitates the sequence assignment, but is in no way crucial to this invention. For peptides that have C-terminal lysine and arginine residues, such as tryptic peptides, their product-ion spectra also contain prominent $[y_n+H+Ag]^+$ ions that may be used to confirm residues cleaved from the C terminus. A m/z value of the $[b_n-H+Ag]^+$ ion and that of a corresponding $[y_n+H+Ag]^+$ ion resulting from cleavage of the same peptide bond are linked by the following relationship: $[y_n+H+Ag]^+=[M+Ag]^++Ag^+-[b_n-H+Ag]^+$. The observation of the corresponding $[y_n+H+Ag]^+$ ions increases the confidence of the assignment for those peptides.

Having generally described the invention, the same will be more readily understood through reference to the following examples which are provided by way of illustration, which are not intended to be limiting of the present invention.

EXAMPLES

GENERAL METHOD AND MATERIALS FOR THE EXAMPLES

Mass Spectrometry. Experiments were conducted on two PE SCIEX triple quadrupole mass spectrometers, an API 365 and an API 3000 prototype (Concord, Ontario). All but one oligopeptide were commercially available (Sigma, St. Louis, Mo.). Samples were typically 2 μM peptides in 50/50 water/methanol containing 10 μM silver nitrate (Aldrich, St. Louis, Mo.). These were continuously infused by means of a syringe pump (Harvard Apparatus, Model 22, South Natick, Mass.) at a typical flow rate of 2 μL/min into the pneumatically assisted electrospray probe with air being the nebulizing gas. The optimum probe position was established from time to time but was typically with the tip about 2 cm from the interface plate and with the spray off-axis from the orifice. Mass spectra were acquired in the positive ion detection mode with unit mass resolution at a step size of 0.1 m/z unit and at a dwell time of 10 ms/step. Typically, 10 scans were summed to produce a mass spectrum. Tandem mass spectrometry was performed with a nitrogen pressure of approximately 3 mTorr in q2 and at a collision energy at the center-of-mass frame ($E_{cm}$) typically of 1–3 eV.

Bovine cytochrome c and ubiquitin were digested in the following manner (Matsudaira (1993)). A 1-mg quantity of protein was dissolved in 100 μL of 8M urea; 40 μL of 0.8M ammonium carbonate was added, followed by 22 μL of 2 mg/mL trypsin. The solution was incubated at 37° C. for 24 h. Water was added to make up the volume to 1 mL. Ten microliters of glacial acetic acid was added. The tryptic digest was subsampled; silver nitrate was added, to result in a final concentration of approximately 10 μM. Two μL of the sample was loaded via a GelLoader tip (1–10 μL, Eppendorf, Hamburg, Germany) into a nanospray probe (Wilm et al. (1994)) (Protana, Odense, Denmark) for electrospraying and sequencing.

Sequencing. For sequencing, product-ion spectra of the $[M+Ag]^+$ ion were collected under $E_{cm}$=1.5, 2.0, 2.5, and 3.0 eV. The values were summed to yield a composite spectrum. These spectra exhibited a wide range of abundant product ions. As an alternative approach, product-ion spectra were acquired with a linear m/z-dependent $E_{cm}$ function to maximize the number of observable sequence-relevant product ions. For sequencing, the peak abundance file of the spectrum were treated to eliminate peaks below a certain user-defined threshold. These treated spectra were read into a custom search algorithm written in Visual Basic which looked for the triplet peak pattern of $(m/z)_1$, $(m/z)_2$=$(m/z)_1$–18.0, and $(m/z)_3$=$(m/z)_2$–28.0 as well as the doublet pattern of $(m/z)_2$ and $(m/z)3$, all to within ±0.5 m/z unit. Triplet and doublet peak patterns that were found were imported into Excel. A user-defined threshold (typically 10% of maximum) was used to filter out noise. The differences in m/z values of neighboring triplets were used to search for cleaved amino acid residues or combinations of them by means of AminoCal.

However, manual sequencing beyond this limit is possible in some favorable cases although the emphasis is the automated search characteristics of the triplet pattern of product-ion peaks.

Example 1

FIG. 1 shows that the product-ion spectra of the $[M+^{107}Ag]^+$ ion (silver has two stable isotopes, $^{107}$Ag and $^{109}$Ag, of almost equal abundance; the product-ion spectra shown in this article will be those of either one of the two isotopes) of leucine enkephalin, YGGFL (SEQ. ID. NO. 1), collected under different $E_{cm}$s: (a) 1.5, (b) 2.0, and (c) 2.5 eV; (d) is the composite of (a), (b), and (c). It is well-known that individual product-ion yield is strongly dependent on collision energy (Dawson et al. (Org. Mass Spectrom. 17, 205–211 (1982); Dawson et ala. (Org. Mass Spectrom. 212–217 (1982)); a necessary step in sequencing is to acquire product-ion spectra under several collision energies to find the best spectra for sequencing. Summing the spectra to produce a composite provides a convenient way of presenting a minimal number of searchable mass spectra to the triplet/doublet identification algorithm. An alternative method to generate a wide range of searchable product ions is to acquire a product-ion spectrum with m/z-dependent $E_{cm}$ function. FIG. 2 shows such a product-ion spectrum also for the $[M+^{107}Ag]^+$ ion of leucine enkephalin. It was acquired with a linear $E_{cm}$ function from 2.5 eV for m/z=30 to 1.5 eV for m/z=663, but otherwise under the same experimental conditions as those in FIG. 1 (the scan time equalled the total scan time of the three individual $E_{cm}$s). It is readily apparent that the spectra are not identical (due to differences in exact collision energies), but the overall spectral quality of the two is similar.

FIGS. 1d and 2 are of such quality that the amino acid sequence of leucine enkephalin can be read directly. The search algorithm looks for a triplet pattern of peaks, whose members are 18 and 28 m/z units apart, and assigns these as $[b_n+OH+Ag]^+$, $[b_n-H+Ag]^+$, and $[a_n-H+Ag]^+$, in decreasing m/z values (the product ions are labeled as b*, b, and a, respectively, in the figures). The amino acid residues that are cleaved from the C terminus can be determined from the differences in the m/z values of the $[M+Ag]^+$ ion and the appropriate triplet members. For example, in FIG. 2 the first triplet that may be identified starting from m/z 662.2 is m/z 548.9, 531.2, and 503.1 (differences of m/z values, Δm/z= 17.7 and 28.1). The peak with the largest m/z value in the triplet is the $[b_n+OH+Ag]^+$ ion, which is a truncated peptide after cleavage of the C-terminal residue (Chu et al. (not published)). The difference in m/z values between the $[M+Ag]^+$ ion and the $[b_n+OH+Ag]^+$ ion is 662.2–548.9 ) 113.3, thus identifying leucine or isoleucine (theoretical Δm/z=113.1) as the C-terminal residue that is cleaved. The second triplet that is identifiable is m/z 402.1, 384.0, and 356.1 (Δm/z=18.1 and 28.3). The difference in m/z values between the $[b_n+OH+Ag]^+$ ion of the first triplet and the $[b_n+OH+Ag]^+$ ion of this second triplet (i.e., the $[b_n-1+OH+Ag]^+$ ion) is 548.9–402.1=146.8, which identifies the residue preceding the C terminus as phenylalanine (theoretical Δm/z=147.1). The third triplet identified is m/z 345.0, 327.0, and 299.1 (Δm/z=18.0 and 27.9). The difference between the m/z value of the $[b_{n-1}+OH+Ag]^+$ ion of the preceding triplet and that of the $[b_{n-2}+OH+Ag]^+$ ion of this triplet is 402.1–345.0=57.1, which identifies the third residue from the C terminus as glycine (theoretical Δm/z=57.0). The triplet pattern disappears on further decreasing m/z, and the search algorithm reaches its application limit.

The last triplet peak identified has a m/z value of about 300. This signifies it is likely the first two amino acid residues from the N terminus for m/z<300, which means that the third peak of the last triplet, m/z=299.1, is the $[a_2-H+Ag]^+$ ion. Cleavage of the peptide linkage between the N-terminal and the second residues produces the n=1 series of product ions; however, the $[b_n-H+Ag]^+$ ion does not typically exist as most b ions are oxazolones, which are composed of a minimum of two residues, and the $[b_1+OH+Ag]^+$ ion is almost always absent (Yalcin et al. (1995); Yalcin et al. (1996); Ambihapathy et al. (1997); Nold et ala. (1997); Lee et al. (J. Am. Chem. Soc. 1998). The only abundant product ion typically seen from the cleavage between the N-terminal and the second residues is the $[a_1-H+Ag]^+$ ion, which is assigned to the peak at m/z=242.1. The difference in m/z values between the $[a_2-H+Ag]^+$ and the $[a_1-H+Ag]^+$ ions is 299.1–242.1=57.0, which identifies the second residue (or the fourth residue from the C terminus) as, again, glycine. The identity of the N-terminal residue is found by subtracting the difference between the m/z values of the silver isotope and the proton, 106.9–1.0=105.9 in this example, from the m/z value of the $[a_1-H+Ag]^+$ ion, 242.1–105.9=136.2, which identifies it as the immonium ion of tyrosine (theoretical Δm/z=136.2). Thus, the determined amino acid sequence of leucine enkephalin is Y-G-G-F-L/I, which is correct.

EXAMPLE 2

Figure 3:
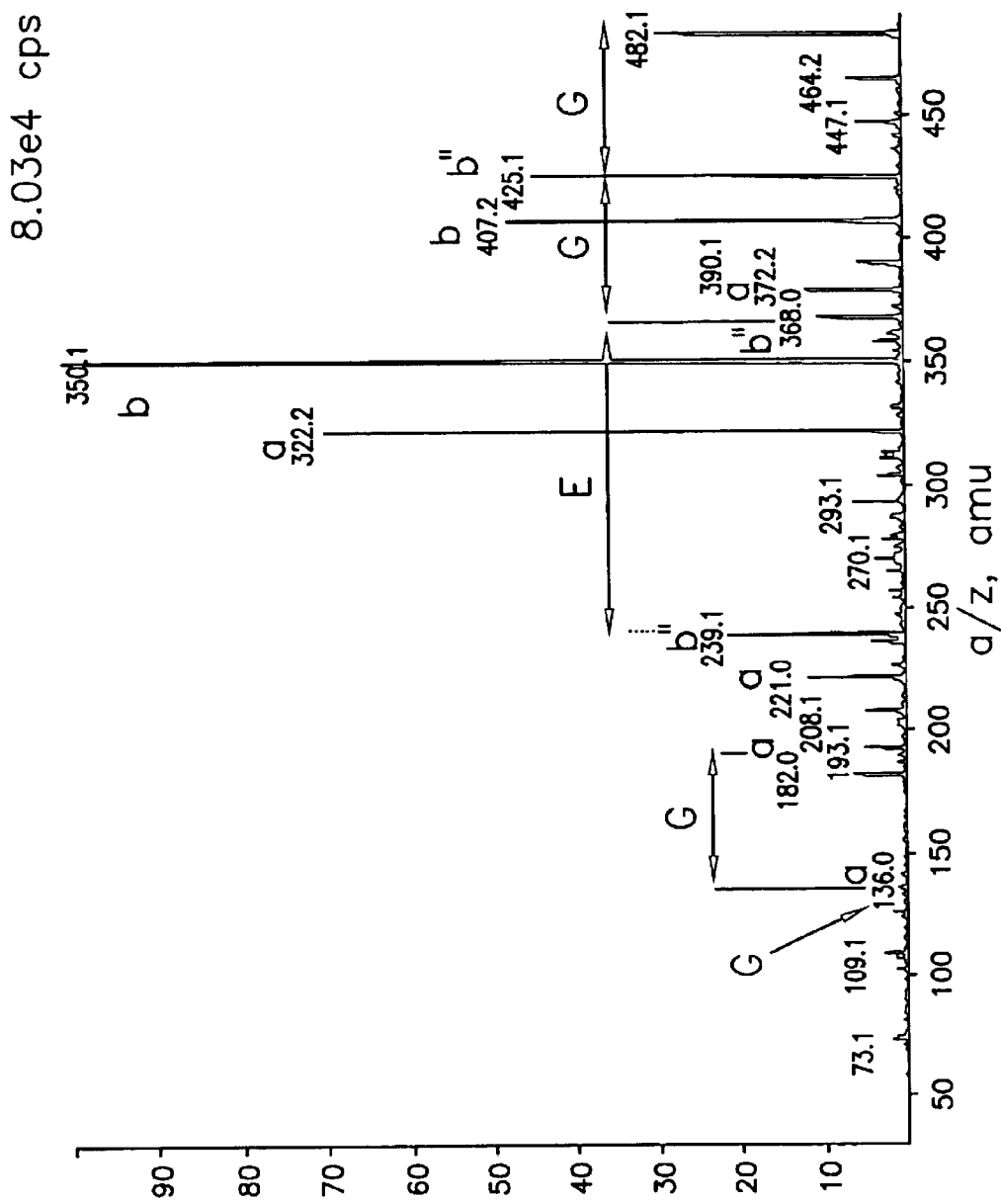
FIG. 3 shows a product-ion spectrum of the [M+$^{107}$Ag]$^+$ ion of GGEGG (SEQ. ID. NO. 2) at an E$_{cm}$ of 2.0 eV.

FIG. 3 shows a product-ion spectrum of the $[M+^{107}Ag]^+$ ion of GGEGG (SEQ. ID. NO. 2), glycylglycylglutamylglycylglycine. Sequencing of the argentinated peptide is straightforward and similar to that discussed in Example 1 for leucine enkephalin. The difference in m/z values between the $[M+^{107}Ag]^+$ ion and the first $[b_n+OH+Ag]^+$ ion is 482.1–425.1=57.0, which identifies the C-terminal residue as glycine (theoretical Δm/z 57.0). The difference in m/z values between the first $[b_n+OH+Ag]^+$ and the second $[b_n+OH+Ag]^+$ is 425.1−368.0=57.1; this identifies the residue preceding the C-terminus as, again, glycine. Repeating the procedure yields the next residue, glutamic acid (experimental $\Delta m/z=128.9$ versus theoretical $\Delta m/z=129.0$). The triplet peak pattern disappears beyond glutamic acid; however, manual interpretation reveals further sequence information. The $[a_1-H+Ag]^+$ in this product-ion spectrum is weak. However, the small m/z value of the $[a_1-H+Ag]^+$ ion of the last triplet, 193.1, strongly suggests that it is the $[a_1-H+Ag]^+$ ion. This makes G-G as the only possible option for the N-terminal and second residues (theoretical m/z=193.0). Furthermore, FIG. 3 shows a small peak at m/z 136.0, which is assignable as the $[a_1-H+Ag]^+$ ion (theoretical m/z=136.0, assuming the first residue is glycine). Thus, the determined sequence is G-G-E-G-G (SEQ. ID. NO. 2).

EXAMPLE 3

Figure 4:
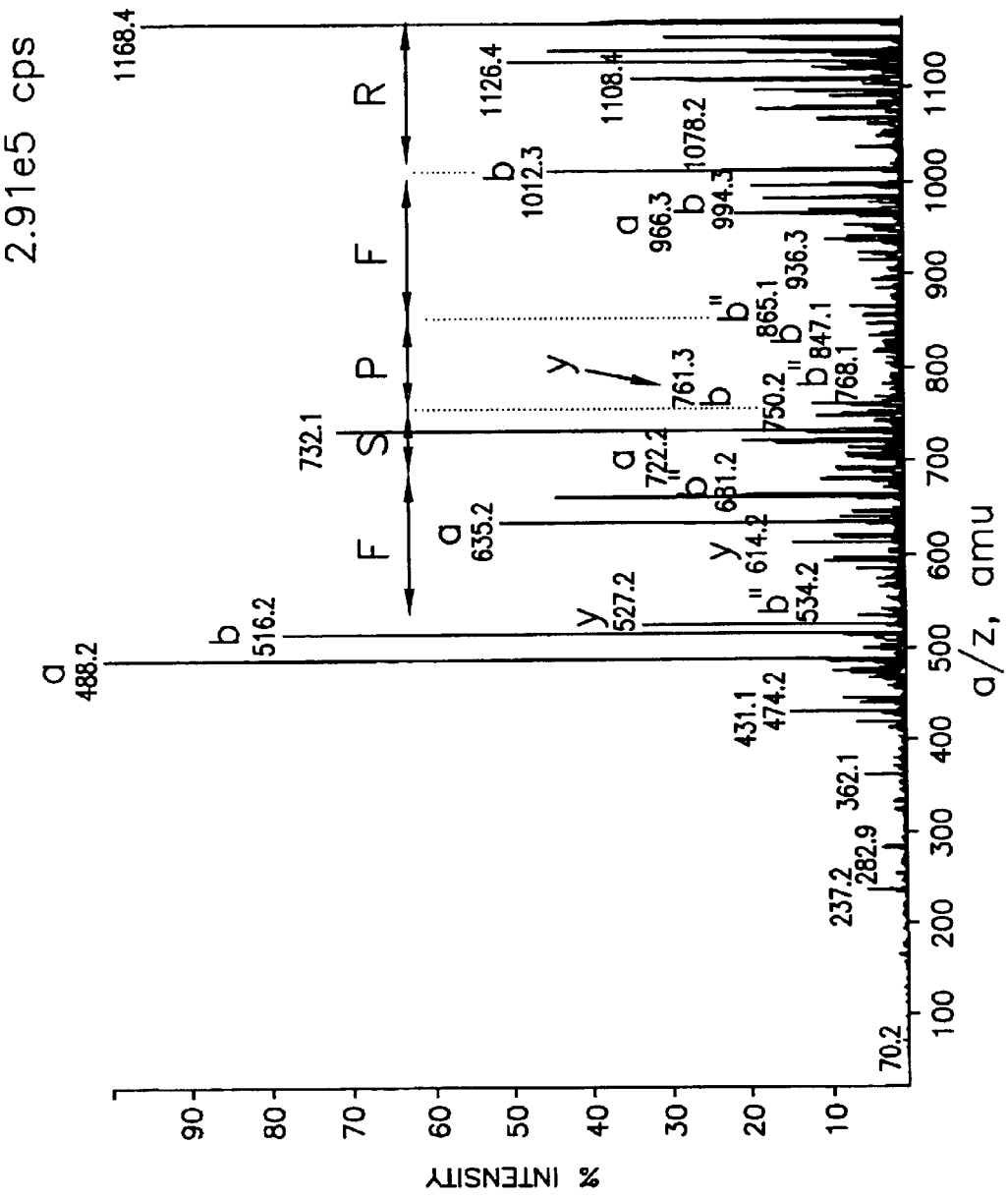
FIG. 4 shows the composite product-ion spectrum of the [M+$^{107}$Ag]$^+$ ion of bradykinin, RPPGFSPFR (SEQ. ID. NO. 3), at E$_{cm}$ s of 2.0 and 2.5 eV.

The following example relates to a longer peptide bradykinin. A product ion spectrum of the $[M+^{109}Ag]^+$ ion of bradykinin, RPPGFSPFR (SEQ. ID. NO. 3), is shown in FIG. 4. Sequencing of the $[M+H]^+$ ion of bradykinin is considered difficult because the external proton is believed to be sequestered by the highly basic guanidine groups on the side chains of the two arginine residues, thus rendering it unavailable for binding to the amidic functional groups and inducing charge-proximal fragmentation along the peptide backbone (Alexander et al. (1990); Tang et al. (1993); Burlet et al. (1992); Cox et al. (1996); Summerfield et al. (1997)). The Ag+ion, however, appears to bind to many different sites on the peptide, as evident from the relative richness of the fragmentation pattern in FIG. 4. Table 1 summarizes the triplets found and the residues identified using the above approach. It is apparent that only a partial sequence of five residues starting from the C-terminal end of the peptide has been solved-FSPFR (SEQ. ID. NO. 3); the major advantage of sequencing argentinated peptides relative to protonated peptides is the triplet relationship which greatly facilitates product-ion assignment. Bradykinin has the highly basic arginine as its C-terminal residue, which also binds strongly to the silver ion (Lee at al. *J. Am. Soc. Mass Spectrom.* (1998)). In fact, it is our observation that peptides that have C-terminal methionine, lysine, and arginine residues tend to yield relatively strong $[y_n+H+Ag]^+$ product ions (Li et al. (1997); Chu et al. (not published)). In the search algorithm, presence of the corresponding $[y_n+H+Ag]^+$ ion is used as confirmation of the cleaved residue. For bradykinin, the $[y_n+H+Ag]^+$ ions for n=3−5 have been observed (FIG. 4 and Table 1), which confirms results of the triplet search. In FIG. 4, the triplet signal corresponding to cleavage of the proline residue is weak; this is actually a confirmation of the proline-residue assignment. Proline is the only residue from which an oxazolone $[b_n-H+Ag]^+$ cannot be formed and of which the relatively weak $[b_n-H+Ag]^+$ ion is believed to be a ketene (Lee et al., 1. *Am. Chem. Soc.* (1998)). The assignment of praline can often be confirmed by the presence of the appropriate $[y_n+H+Ag]^+$ ions or the identification of the next triplet; the difference in the m/z values of the $[b_n+H+Ag]^+$ ions for n=1 and n=3 is 1010.3−766.5=243.8, which can only mean a combination of cleavage of phenylalanine and proline.

EXAMPLE 4

Figure 5:
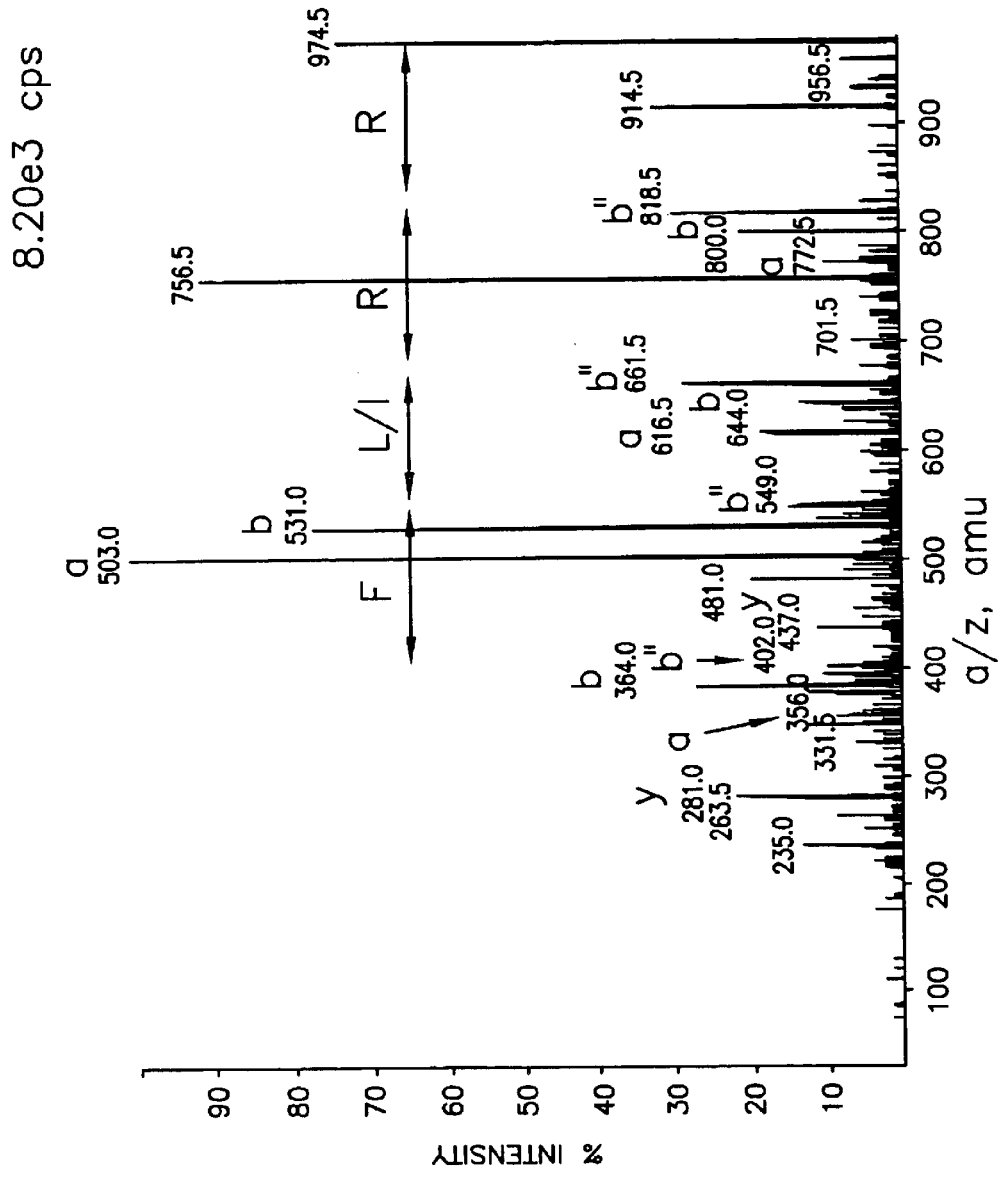
FIG. 5 shows a product-ion spectrum of the [M+$^{107}$Ag]$^+$ ion of dynorphin A fragment 1-7, YGGFLRR (SEQ. ID. NO. 4), at E$_{cm}$=1.9 eV.

FIG. 5 shows a product-ion spectrum of the $[M+^{107}Ag]^+$ ion of dynorphin A fragment 1-7, YGGFLRR (SEQ. ID. NO. 4), another highly basic peptide. The triplets and the residues identified using the search algorithm are tabulated in Table 2. Again, the partial sequence determined, —FLRR, is confirmed by the presence of the appropriate $[y_n+H+Ag]^+$ ions.

Example 5

A frequent and valid criticism of the above type of examples is that it is relatively easy to sequence a peptide whose identity is known a priori. One of us (IKC) was presented with tryptic digests of proteins unknown to him. He was asked to sequence a number of the tryptic peptides from approximately 5 µL of digests using nanospray ionization. Table 3 shows the sequences of the tryptic peptides determined using the search algorithm of the present invention and the sequences subsequently revealed to the experimenter; in all cases, the partial sequences determined were correct. FIG. 6 shows two of the product-ion spectra obtained to illustrate the quality of the sequence data; the presence of the three triplet series of peaks plus the $[y_n+H+Ag]^+$ series facilitate sequencing and increase the confidence in assignment.

DISCUSSION OF EXAMPLES

The greatest potential for application of sequencing argentinated oligopeptides that we envisage is in the area of automated sequence tag analysis in proteomics, where accurate automatic peak, and subsequently residue, assignment can be made because of the presence of four series of peaks, the $[b_n+OH+Ag]^+$, $[b_n-H+Ag]^+$, $[a_n-H+Ag]^+$, and $[y_n+H+Ag]^+$ ions, and identification of only three or four residues are needed for often unambiguous searches (Shevchenko et al. (1996); Figeys et al. (1996)). Indeed, inputting the partial sequences shown in FIG. 6, together with the bracketing m/z values of the b ions for the corresponding protonated product ions (for FIG. 6a, they are 335.2+1−108.9=227.3 and 610.1+1−108.9=502.2; thus the sequence tag search parameters are 227.3/F/A/G/502.2 for this tryptic peptide) plus the peptide mass (the m/z value of the precursor ion minus 108.9) and the molecular mass of the protein (the m/z value of the $[M+^{109}Ag]^+$ ion of the protein prior to trypsin digestion minus 108.9, which was measured in a separate experiment and provided to the analyst) unambiguously identifies the protein as bovine ubiquitin after a search using Peptide Scan (PE SCIEX) with sequence index files (database) downloaded from the European Molecular Biology Laboratory ftp.embl-heidlberg.de (pub/databases/nrdb/). The results are summarized in Table 4. All the proteins are ubiquitin; swiss/p02248, bovine ubiquitin has the best match with the measured protein molecular mass (Mr) of 8565 Da and has the correct sequence as subsequently revealed.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Sequencing Results for Bradykinin

| trip-let | $[b_n + OH + Ag]^+$ (m/z) | $[b_n - H + Ag]^+$ (m/z) | $[a_n - H + Ag]^+$ (m/z) | residue cleaved | residue assigned | confirmed $[y_n + H + Ag]^+$ |
|---|---|---|---|---|---|---|
| 0 | 1168.4[a] | NA[b] | NA | 156.1 | R | |
| 1 | 1012.3 | 994.3 | 966.3 | 147.0c | F | |
| 2 | 865.0 | 847.1 | 819.9d | 97.2 | P | 5272. |
| 3 | 768.1 | 750.2 | 722.2 | 87.0 | S | 614.2 |
| 4 | 681.2 | 663.1 | 635.2 | 147.0 | F | 761.3 |
| 5 | 534.2 | 516.2 | 488.2 | | | |

[a]$[M + {}^{109}Ag]^+$.
[b]Not applicable.
c[(1012.3 − 865.0) + (994.3 − 847.1) + (966.3 − 819.9)]/3.
dWeak $[b_n - H + Ag]^+$ and $[a_n - H + Ag]^+$ ions due to proline residue (see text for details).

TABLE 2

Sequencing Results for Dynorphin A Fragment 1-7[a]

| trip-let | $[b_n + OH + Ag]^+$ (m/z) | $[b_n - H + Ag]^+$ (m/z) | $[a_n - H + Ag]^+$ (m/z) | residue cleaved | residue assigned | confirmed $[y_n + H + Ag]^+$ |
|---|---|---|---|---|---|---|
| 0 | 974.5 | NA | NA | 156.0 | R | 281.0 |
| 1 | 818.5 | 800.0 | 772.5 | 156.3 | R | 437.0 |
| 2 | 661.5 | 644.0 | 616.5 | 113.0 | L/I | 550.0 |
| 3 | 549.0 | 531.0 | 503.0 | 147.0 | F | |
| 4 | 402.0 | 384.0 | 356.0 | | | |

[a]See Table 1 for explanation of details.

TABLE 3

Sequencing of Tryptic Peptides

| peptide | determined sequence | actual sequence |
|---|---|---|
| 1 | -FAGK (SEQ. ID. NO. 6) | LIFAGK (SEQ. ID. NO. 7) |
| 2 | -(L/I)FVK (SEQ. ID. NO. 8) | MQIFVK (SEQ. ID. NO. 9) |
| 3 | -TGK (SEQ. ID. NO. 10) | TLTGK (SEQ. ID. NO. 11) |
| 4 | -DVEK (SEQ. ID. NO. 12) | GDVEK (SEQ. ID. NO. 13) |
| 5 | -V(Q/K)K$_a$ (SEQ. ID. NO. 14) | IFVQK (SEQ. ID. NO. 15) |

[a]K and Q are isobaric; however, since trypsin cleaves only on the C-terminal side of K and R, the identity of the C-terminal residue is unambiguous, but that of preceding residues is not.

TABLE 4

Sequence Tag Analyses of Tryptic Peptides
(Protein Molecule Mass: 8565 Da)

(a) Peptide mass: 647.2 Da (756.1−108.9)
    Sequence tag: 227.3/FAG/502.2
    (335.2 + 1 − 108.9 = 227.3;
(b) 610.1 + 1 − 108.9 = 502.2)
    Peptide mass: 764.4 Da (873.3 − 108.9)
    Sequence tag: 260.1/L (or I) FV/619.1
    (368.0 + 1 − 108.9 = 260.1;
    727.0 + 1 − 108.9 = 619.1)

| Protein | Mr |
|---|---|
| swiss \| P02248 | 8564.87 |
| spit \| Q17001 | 8563.89 |
| spit \| Q41405 | 8562.83 |
| t \| M21581 | 8566.91 |
| t \| M22218 | 8566.91 |

Swiss | P02248, bold sections correspond to the tryptic peptides entered for the search and identification MQIFVKTLTGKTITLEVEPSDTIEN-VKAKIQDKEGIPPDQQRLIFAGKQLE DGRTLSDY-NIQKESTLHLVLRLRGG (SEQ. ID. NO. 16)

FULL CITATIONS FOR REFERENCES REFERRED TO IN THE SPECIFICATION

Alexander, A. J.; Thibault, P.; Boyd, R. K.; Curtis, J. M.; Rinehart, K. L. Int. J. Mass Spectrom. Ion Processes 1990, 98, 107–134.

Ambihapathy, K.; Yalcin, T.; Leung, H.-W.; Harrison, A. G. J. Mass Spectrom. 1997, 32, 209–215.

Bouchonnet, S.; Hoppilliard, Y. Org. Mass Spectrom. 1992, 27, 71–76.

Burlet, O.; Orkiszewski, R. S.; Ballard, K. D.; Gaskell, S. J. Rapid Commun. Mass Spectrom. 1992, 6, 658–662.

Cantor, C. R.; Schimmel, P. R. Biophysical Chemistry; W. H. Freeman and Co.: San Francisco, 1980.

Chu, I. K.; Lee, V. W.-M.; Rodriquez, C. F.; Lau, T.-C.; Hopkinson, A. C.; Siu, K. W. M., manuscript in preparation.

Cox, K. A.; Gaskell, S. J.; Morris, M.; Whiting, A. J. Am. Soc. Mass Spectrom. 1996, 7, 522–531.

Dawson, P. H.; French, J. B.; Buckley, J. A.; Douglas, D. J.; Simmons, D. Org. Mass Spectrom. 1982, 17, 205–211.

Dawson, P. H.; French, J. B.; Buckley, J. A.; Douglas, D. J.; Simmons, D. Org. Mass Spectrom. 1982, 17, 212–217.

Deng, H.; Kebarle, P. J. Phys. Chem. A 1998, 102, 571–579.

Dongré, A. R.; Somogyi, Á.; Wysocki, V. H. J. Mass Spectrom. 1996, 31, 339–350.

Dongré, A. R.; Jones, J. L.; Somogyi, Á.; Wysocki, V. H. J. Am. Chem. Soc. 1996, 118, 8365–8374.

Edman, P. Mol. Biol. Biochem. Biophys. 1970, 8, 211–255.

Fenn, J. B.; Mann, M.; Meng, C. K.; Wong, S. F.; Whitehouse, C. M. Science 1989, 246, 64–71.

Figeys, D.; van Oostveen, I.; Ducret, A.; Aebersold, R. Anal. Chem. 1996, 68, 1822–1828.

Grese, R. P.; Cerny, R. L.; Gross, M. L. J. Am. Chem. Soc. 1989, 111, 2835–2842.

Grese, R. P.; Gross, M. L. J. Am. Chem. Soc. 1990, 112, 5098–5104.

Hu, P.; Gross, M. L. J. Am. Chem. Soc. 1992, 114, 9153–9160.

Hu, P.; Gross, M. L. J. Am. Soc. Mass Spectrom. 1993, 5, 137–143.

Hu, P.; Gross, M. L. J. Am. Chem. Soc. 1993, 115, 8821–8828.

Hunt, D. F.; Yates, J. R., III; Shabanowitz, J.; Winston, S.; Hauer, C. R. Proc. Natl. Acad. Sci. 1986, 83, 6233–6237.

Johnson, R. S.; Martin, S. A.; Bieman, K. Int. J. Mass Spectrom. Ion Processes 1988, 86, 137–154.

Jones, J. L.; Dongré, A. R.; Somogyi, Á.; Wysocki, V. H. J. Am. Soc. Chem. 1994, 116, 8368–8369.

Klassen, J. S.; Anderson, S. G.; Blades, A. T.; Kebarle, P. J. Phys. Chem. 1996, 100, 14218–14227.

Leary, J. A.; Williams, T. D.; Bott, G. Rapid Commun. Mass Spectrom. 1989, 3, 192–196.

Leary, J. A.; Zhou, Z.; Ogden, S. A.; Williams, T. D. J. Am. Soc. Mass Spectrom. 1990, 1, 473–480.

Lee, S.-W.; Kim, H. S.; Beauchamp, J. L. J. Am. Chem. Soc. 1998, 120, 3188–3195.

Lee, V. W.-M.; Li, H.; Lau, T.-C.; Guevremont, R.; Siu, K. W. M. J. Am. Soc. Mass Spectrom. 1998, 9, 760–766.

Lee, V. W.-M.; Li, H.; Lau, T.-C.; Siu, K. W. M. J. Am. Chem. Soc. 1998, 120, 7302–7309.

Li, H.; Siu, K. W. M.; Guevremont, R.; Le Blanc, J. C. Y. J. Am. Soc. Mass Spectrom. 1997, 8, 781–792.

Matsudaira, P., Ed. A Practical Guide to Protein and Peptide Purification for Microsequencing, 2nd ed.; Academic Press: San Diego, 1993; pp 37–39. Analytical Chemistry, Vol. 71, No. 13, Jul. 1, 1999 2365

McCormack, A. L.; Somogyi, Á.; Dongré, A. R.; Wysocki, V. H. Anal. Chem. 1993, 65, 2859–2872.

McLafferty, F. W. Science 1981, 214, 280–287.

Narula, S. S.; Mehra, R. K.; Winge, D. R.; Armitage, I. M. J. Am. Chem. Soc. 1991, 113, 9354–9358.

Nold, M. J.; Wesdemiotis, C.; Yalcin, T.; Harrison, A. G. Int. J. Mass Spectrom. Ion Processes 1997, 164, 137–153.

Papayannopoulos, I. A. Mass Spectrom. Rev. 1995, 14, 49–73.

Renner, D.; Spiteller, G. Biol. Environ. Mass Spectrom. 1988, 15, 75–77. Anal. Chem. 1999, 71, 2364–2372

Shevchenko, A.; Jensen, O. N.; Podtelejnikov, A. V.; Sagliocco, F.; Wilm, M.; Vorm, O.; Mortensen, P.; Shevchenko, A.; Boucherie, H.; Mann, M. Proc. Natl. Acad. Sci. U.S.A. 1996, 93, 14440–14445.

Smith, R. D.; Loo, J. A.; Ogorzalek Loo, R. R.; Busman, M.; Udseth, H. R. Mass Spectrom. Rev. 1991, 10, 359–451.

Stillman, M. J.; Presta, A.; Gui, Z.; Jiang, D.-T. In Metal-Based Drugs; Gielen, M., Ed.; Freund: London, 1994; Vol. 1, pp 375–393.

Summerfield, S. G.; Whiting, A.; Gaskell, S. J. Int. J. Mass Spectrom. Ion Processes 1997, 162, 149–161.

Tang, X.; Ens, W.; Standing, K. G.; Westmore. J. B. Anal. Chem. 1988, 60, 1791–1799.

Tang, X.-J.; Thibault, P.; Boyd, R. K. Anal. Chem. 1993, 65, 2824–2834.

Teesch, L. M.; Adams, J. J. Am. Chem. Soc. 1990, 112, 4110–4120.

Teesch, L. M.; Adams, J. J. Am. Chem. Soc. 1991, 113, 812–820.

Teesch, L. M.; Orlando, R. C.; Adams, J. J. Am. Chem. Soc. 1991, 113, 3668–3675.

Wilm, M. S.; Mann, M. Int. J. Mass Spectrom. Ion Proc. 1994, 136, 167–180.

Yalcin, T.; Khouw, C.; Csizmadia, I. G.; Peterson, M. R.; Harrison, A. G. J. Am. Soc. Mass Spectrom. 1995, 6, 1165–1174.

Yalcin, T.; Csizmadia, I. G.; Peterson, M. R.; Harrison, A. G. J. Am. Soc. Mass Spectrom. 1996, 7, 233–242.

Zhao, H.; Reiter, A.; Teesch, L. M.; Adams, J. J. Am. Chem. Soc. 1993, 115, 2854–2863.

---

We claim:

1. A method of analyzing argentinated peptides or argentinated proteins using mass spectrometry comprising: (a) combining an oligopeptide with silver to provide a sample comprising argentinated peptide; (b) submitting the sample to a mass spectrometer; (c) performing scans of silver containing peaks in optimum collision energies to maximize doublet or triplex peak patterns, wherein the scans are performed; (i) under increasing collision energies, identifying doublet and triplet peak patterns and determining the collision energies that maximized the doublet and/or triplet peak patterns, summing the spectra information from said optimum collision energies to produce a composite spectra that maximizes the doublet and/or triplet peak patterns: or (ii) over a range of collision enemies to maximize the doublet and/or triplet peak patterns; (d) identifying any doublet or triplet peak pattern; (e) confirming with Y ions; and (f) determining partial sequence by the mass separation between two successive doublet or triplet patterns.

2. A method according to claim 1 wherein the performing scans comprises collecting product ion spectra of the [M+Ag]$^+$ ion, where M=oligopeptide.

3. A method according to claim 1 wherein the oligopeptide consists of from about 3 to about 10 amino acids.

4. A method according to claim 1 wherein the silver is silver nitrate.

5. A method according to claim 1, wherein the step of determining partial sequence by the mass separation between two successive doublet or triplet patterns further comprises searching for, and identifying cleaved amino acid residues based on differences in m/z values of neighboring triplets where the m/z value of the $[b_n-H+Ag]^+$ ion and the corresponding $[y_n+H+Ag]^+$ ion are related by formula $[y_n+H+Ag]^+=[M+Ag]^++Ag^+-[b_n-H+Ag]^+$.

6. A method according to claim 5 wherein the searching and identifying is conducted by a custom search algorithm.

7. A method according to claim 6 wherein the algorithm is written in Visual Basic and identifies both the triplet peak pattern of $(m/z)_1$, $(m/z)_2=(m/z)_1-18.0$, and $(m/z)_3=(m/z)_2-8.0$ as well as the doublet pattern of $(m/z)_2$ and $(m/z)_3$, all to within±0.5 m/z unit.

8. A method according to claim 2, wherein product ion spectra of the [M−Ag]$^+$ion me collected under $E_{cm}$s, of 1.5, 2.0, 2.5 and 3.0 eV.

9. A method according to claim 1 wherein the mass spectrometer is a triple quadrupole mass spectrometer, two triple quadrupole mass spectrometers, a quadrupole/time-of-flight mass spectrometer, an ion-trap mass spectrometer, or a time-of-flight mass spectrometer amenable to post-source decay or collision-induced dissociation.

10. A method of analyzing argentinated peptides or argentinated proteins using mass spectrometry comprising: (a) combining an oligopeptide with silver nitrate in solution; (b) submitting a sample of the solution to a mass spectrometer; (c) collecting product ion spectra of the [M+Ag]$^-$ion, where M=oligopeptide; (d) identifying a triplet peak pattern; (a) identifying a doublet peak pattern; and (f) searching for, and identifying cleaved amino acid residues based on differences in m/z values of neighboring triplets where the m/z value of the $[b_n-H+Ag]^+$ ion and the corresponding $[y_n+H+Ag]^+$ ion are related by the formula:

$$[y_n+H+Ag]^+=[M+Ag]^++Ag^+-[b_n-H+Ag]^+.$$

11. A method according to claim 10 wherein the oligopeptide consists of from about 3 to about 10 amino acids.

12. A method according to claim 10 wherein the searching and identifying is conducted by a custom search algorithm.

13. A method according to claim 12 wherein the algorithm is written in Visual Basic and looks for the triplet peak pattern of $(m/z)_1$, $(m/z)_2=(m/z)_1-18.0$, and $(m/z)_3=(m/z)_2-28.0$ as well as the doublet pattern of $(m/z)_2$ and $(m/z)_3$, all to within±0.5 m/z unit.

14. A method according to claim 10 wherein product ion spectra of the [M+Ag]$^+$ ion are collected under $E_{cm}$s, of 1.5, 2.0, 2.5 and 3.0 eV.

15. A method according to claim 10 wherein the mass spectrometer is a triple quadrupole mass spectrometer, two triple quadrupole mass spectrometers, a quadrupole/time-of-flight mass spectrometer, an ion-trap mass spectrometer, or a time-of-flight mass spectrometer amenable to post-source decay or collision-induced dissociation.

* * * * *

SEQUENCE LISTING

<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: leucine enkephalin

<400> SEQUENCE: 1

Tyr Gly Gly Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: glycylglycylglutamylglycylglycine

<400> SEQUENCE: 2

Gly Gly Glu Gly Gly
1               5

```
<210> SEQ ID NO 3
<211> LENGTH: 9
<212> TYPE: PRT
<213> ORGANISM: Artificial Sequence
<220> FEATURE:
<223> OTHER INFORMATION: bradykinin

<400> SEQUENCE: 3

Arg Pro Pro Gly Phe Ser Pro Phe Arg
1               5

<210> SEQ ID NO 4
<211> LENGTH: 7
<212> TYPE: PRT
<213> ORGANISM: Artificial Sequence
<220> FEATURE:
<223> OTHER INFORMATION: dynorphin A

<400> SEQUENCE: 4

Tyr Gly Gly Phe Leu Arg Arg
1               5

<210> SEQ ID NO 5
<211> LENGTH: 5
<212> TYPE: PRT
<213> ORGANISM: Artificial Sequence
<220> FEATURE:
<223> OTHER INFORMATION: leucine enkephalin
<221> NAME/KEY: MISC_FEATURE
<222> LOCATION: (5)..(5)
<223> OTHER INFORMATION: X is L or I

<400> SEQUENCE: 5

Tyr Gly Gly Phe Xaa
1               5

<210> SEQ ID NO 6
<211> LENGTH: 4
<212> TYPE: PRT
<213> ORGANISM: Bovine ubiquitin

<400> SEQUENCE: 6

Phe Ala Gly Lys
1

<210> SEQ ID NO 7
<211> LENGTH: 6
<212> TYPE: PRT
<213> ORGANISM: Bovine ubiquitin

<400> SEQUENCE: 7

Leu Ile Phe Ala Gly Lys
1               5

<210> SEQ ID NO 8
<211> LENGTH: 4
<212> TYPE: PRT
<213> ORGANISM: Bovine ubiquitin
<220> FEATURE:
<221> NAME/KEY: MISC_FEATURE
<222> LOCATION: (1)..(1)
<223> OTHER INFORMATION: X is L or I

<400> SEQUENCE: 8

Xaa Phe Val Lys
1
```

```
<210> SEQ ID NO 9
<211> LENGTH: 6
<212> TYPE: PRT
<213> ORGANISM: Bovine ubiquitin

<400> SEQUENCE: 9

Met Gln Ile Phe Val Lys
1               5

<210> SEQ ID NO 10
<211> LENGTH: 3
<212> TYPE: PRT
<213> ORGANISM: Bovine ubiquitin

<400> SEQUENCE: 10

Thr Gly Lys
1

<210> SEQ ID NO 11
<211> LENGTH: 5
<212> TYPE: PRT
<213> ORGANISM: Bovine ubiquitin

<400> SEQUENCE: 11

Thr Leu Thr Gly Lys
1               5

<210> SEQ ID NO 12
<211> LENGTH: 4
<212> TYPE: PRT
<213> ORGANISM: Bovine ubiquitin

<400> SEQUENCE: 12

Asp Val Glu Lys
1

<210> SEQ ID NO 13
<211> LENGTH: 5
<212> TYPE: PRT
<213> ORGANISM: Bovine ubiquitin

<400> SEQUENCE: 13

Gly Asp Val Glu Lys
1               5

<210> SEQ ID NO 14
<211> LENGTH: 3
<212> TYPE: PRT
<213> ORGANISM: Bovine ubiquitin
<220> FEATURE:
<221> NAME/KEY: MISC_FEATURE
<222> LOCATION: (2)..(2)
<223> OTHER INFORMATION: X is Q or K

<400> SEQUENCE: 14

Val Xaa Lys
1

<210> SEQ ID NO 15
<211> LENGTH: 5
<212> TYPE: PRT
<213> ORGANISM: Bovine ubiquitin

<400> SEQUENCE: 15

Ile Phe Val Gln Lys
```

-continued

```
<210> SEQ ID NO 16
<211> LENGTH: 76
<212> TYPE: PRT
<213> ORGANISM: Bovine ubiquitin

<400> SEQUENCE: 16

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```